United States Patent [19]

Kaufhold

[11] Patent Number: 4,785,100
[45] Date of Patent: Nov. 15, 1988

[54] PROCESS FOR THE PRODUCTION OF N-SUBSTITUTED MORPHOLINE AND PIPERIDINE DERIVATIVES

[75] Inventor: Manfred Kaufhold, Marl, Fed. Rep. of Germany

[73] Assignee: Huels Aktiengesellshaft, Marl, Fed. Rep. of Germany

[21] Appl. No.: 103,329

[22] Filed: Oct. 1, 1987

[30] Foreign Application Priority Data

Oct. 2, 1986 [DE] Fed. Rep. of Germany ....... 3633520

[51] Int. Cl.$^4$ .................. C07D 265/30; C07D 295/02; C07D 211/14
[52] U.S. Cl. .................................... 544/178; 546/192; 570/197
[58] Field of Search ........................ 546/192; 544/178

[56] References Cited

U.S. PATENT DOCUMENTS 4,241,058 12/1980 Pfiffner ............................. 544/178

FOREIGN PATENT DOCUMENTS 1591267 6/1981 United Kingdom.

Primary Examiner—Robert W. Ramsuer
Attorney, Agent, or Firm—Millen & White

[57] ABSTRACT

A process is provided for the production of N-substituted morpholines and piperidines of the formula

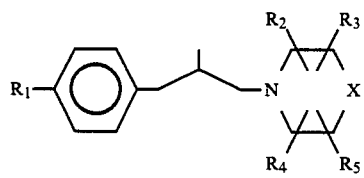

comprising the steps of
(a) reacting a methallylbenzene of the formulas

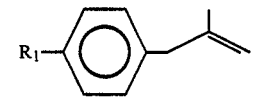

wherein $R_1$ is H or a straight or branched chained $C_1$-$C_4$ alkyl group, alone or in admixture with a corresponding isobutenylbenzene of the formula

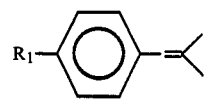

wherein $R_1$ is as defined above, with hydrogen bromide in the presence of a peroxide to yield, respectively, the corresponding bromine compound of the formula

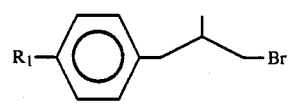

wherein $R_1$ is as defined above, alone or in admixture with a bromine compound of the formula

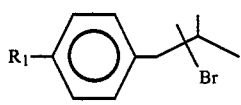

wherein $R_1$ is as defined above and wherein the bromine atom is in the secondary or tertiary position, and
(b) reacting the resultant bromine compound of formula IV, alone or in admixture with the corresponding bromine compound of Formula V, with a compound of the formula

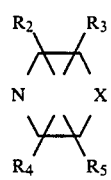

wherein $R_2$, $R_3$, $R_4$ and $R_5$ are each independently hydrogen, methyl or ethyl and X is as indicated above.

15 Claims, No Drawings

PROCESS FOR THE PRODUCTION OF N-SUBSTITUTED MORPHOLINE AND PIPERIDINE DERIVATIVES

BACKGROUND OF THE INVENTION

The invention relates to a two-step process for the production of N-substituted morpholine and piperidine derivatives of the formula

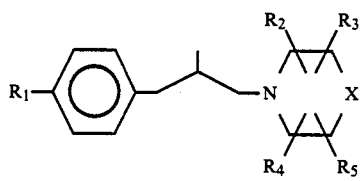

wherein $R_2$, $R_3$, $R_4$ and $R_5$ each is independently hydrogen, methyl or ethyl and X is O or $CH_2$ and to the bromination reaction employed therein.

Conventional syntheses of N-substituted morpholine and piperidine derivatives of Formula I exist. DE-Pat. No. 26 56 747=CA-Pat. No. 1 086 734=GB-Pat. No. 1 591 267 describes a process for the production of morpholine derivates wherein 3-p-tert-butylphenyl-2-methylpropanal is reacted with 2,6-dimethylmorpholine in the presence of formic acid. A disadvantage in this and similar processes is the use of 3-p-tert-butylphenyl-2-methylpropanal which is expensive and which, in turn, is prepared from p-tert-butyl-benzaldehyde, which is technically accessible only with difficulties, by aldolization with propionaldehyde and subsequent selective hydrogenation of the double bond in the aldolization product.

EP-Pat. No. 0 005 541=AU-Pat. No. 79/46909=ZA No. 79/2242 demonstrates that substituted morpholine and piperidine derivates are easily preparable with the aid of bromides corresponding to the following formula (see in this connection, Example 10):

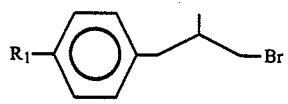

wherein $R_1$ is H or a $C_1$–$C_4$ alkyl group. The bromides, however, are synthesized from the corresponding alcohols with phosphorus tribromide. The alcohols are also prepared in a multistage synthesis starting with p-tert-butylbenzaldehyde which is technically accessible only with difficulties. All known methods for the production of the morpholine and piperidine derivatives of Formula I, which are substituted in the para-position thus start with the expensive and technically poorly accessible p-alkyl benzaldehydes, e.g., p-tert-butylbenzaldehyde.

A process would be desirable which makes possible the preparation of the bromine compounds above starting with inexpensive chemicals in conventional industrial apparatus. There is great interest in such a process by which, with low technical expenditure and without the use of costly reagents, N-substituted morpholine and piperidine derivatives can be produced, because these products have great economic importance, for example, as fungicides (GB-Pat. No. 1 591 267 and DE-No. OS 31 01 233=EP-Pat. No. 0 056 461).

SUMMARY OF THE INVENTION

Accordingly, it is an object of this invention to provide a process for the preparation of N-substituted morpholines and piperidines which is efficient and avoids the disadvantages of the prior art starting materials.

Upon further study of the specification and appended claims, further objects and advantages of this invention will become apparent to those skilled in the art.

In one aspect of the invention these objects have been achieved by providing a process for the production of N-substituted morpholines and piperidines of the formula

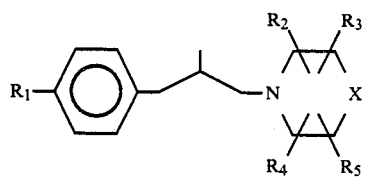

comprising the steps of
(a) reacting a p-alkyl-substituted or an un-substituted methallylbenzene of the formula

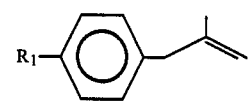

wherein $R_1$ is H or a straight or branched chained $C_1$–$C_4$ alkyl group, alone or in admixture with a corresponding p-alkyl-substituted or un-alkyl-substituted isobutenylbenzene of the formula

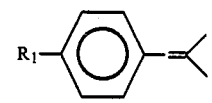

wherein $R_1$ is as defined above, with hydrogen bromide in the presence of a peroxide to yield, respectively, the corresponding bromine compound of the formula

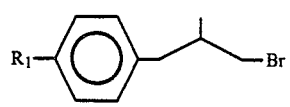

wherein $R_1$ is as defined above, alone or in admixture with a bromine compound of the formula

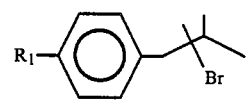

wherein $R_1$ is as defined above and wherein

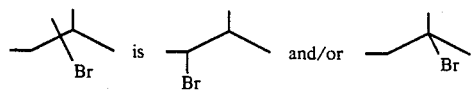

and (b) reacting the resultant bromine compound of formula IV, alone or in admixture with the corresponding bromine compound of Formula V, with a compound of the formula

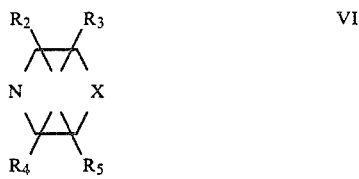

wherein $R_2$, $R_3$, $R_4$ and $R_5$ are each independently hydrogen, methyl or ethyl and X is as indicated above.

DETAILED DISCUSSION

Examples of $R_1$ alkyl groups are methyl, ethyl, propyl, isopropyl, butyl, and tert.-butyl, preferably tert.-butyl. Suitable substituents for groups and $R_4$ are H, $R_3$ and $R_5$ are $CH_3$ or $R_5$ is H and X is O.

Surprisingly, N-substituted morpholine and piperidine derivatives of general Formula I are obtained in good yields of about 80–90% in one step of the synthesis and 70–80% in booth steps and with a high purity of 97–98%, as determined by gas chromatographic analysis, by chemically adding hydrogen bromide to methallylbenzene or to a p-alkyl-substituted methallylbenzene (alpha isomer) (II) in the presence of peroxides and by reacting the thus-produced bromine compound (IV) and (V) with morpholine or piperidine or their derivatives. This effect was unexpected inasmuch as the addition of hydrogen bromide would be expected to yield a number of secondary compounds which would be expected to further react also with morpholine or piperidine and, respectively, their derivatives and lead to impurities in the desired product. It would been expected that a number of secondary compounds would have been obtained, e.g. the problems of addition of HBr on styrene (J. Amer. Chem. Soc. 61, 2693 (1939).

In the addition of HBr on compounds II selectivities of over 90% are generally obtained. Yields of from 80–90% are generally obtained. No strict requirements need to be met regarding the purity of the methallylbenzene (II) or p-alkyl-substituted methallylbenzene utilized.

It has furthermore been surprisingly found that the content of the corresponding isomeric beta-olefin, the isobutenylbenzene and, respectively, the p-alkyl-substituted isobutenylbenzene (III), in methallylbenzene can be arbitrarily high without bringing about a reduction in the purity of the final product. In other words, an olefin mixture of (II) and (III) can be employed, and the end result is solely the reaction product of (II). If a mixture of the compound of formulae II and III is employed, the mixture can contain up to about 80 mole% of the coumpound of formula III.

Consequently, a great advantage of the process according to this invention resides in being able to use industrial olefin mixtures as they are obtained, for example, in the thermal decomposition of neophyl chloride (2-methyl-2-phenylpropyl chloride) and, respectively, p-alkyl-substituted neophyl chlorides (see U.S. Pat. No. 2,454,779). In the process of this patent, cleavage of the chlorine compounds takes place in the presence of alkali salts of carboxylic acids and as a consequence, the isomer ratio or alpha- to beta-olefin is 2:1 to 1:1.

The compounds of Formulae II and III are otherwise difficulty preparable from conventional starting materials.

As an additional, surprising advantage of the process according to this invention, it has been found that the olefin produced from the mixture of tertiary and secondary bromine compounds (V) during the reaction with the nitrogen compounds (VI) is not, as expected, an isobutenylbenzene or substituted morpholine or piperidine derivative but rather a mixture of alpha- and beta-olefins of formulae II and III in an approximate ratio of alpha to beta of 3:4. This mixture can again be reacted with hydrogen bromide according to the process of this invention and directly utilized as starting materials in the process of the invention which is of great utility for the economy of the process. The olefins can be rised from the bromine compounds V heating at a temperature of from 120°–200° C. of up to the reflux temperature of compound VI for a period of 1 to 4 hours, preferably in the presence of compound VI.

The following is important for conducting the method of this invention: the chemical addition of hydrogen bromide to the starting olefin takes place at 0°–20° C. in the presence of a catalytically effective amount of a catalytically effective peroxide, for example, dibenzoyl peroxide, and a nonpolar solvent, such as, for example, hexane, as described for other olefins in the literature: "Methoden der Organischen Chemie" [Methods of Organic Chemistry], Houben Weyl, Georg Thieme Publishers, Stuttgart (1960), V/4: 111. Equivalent, conventional peroxides and solvents are also suitable, e.g. diacetyle peroxide, cumene hydroperoxide, diisopropylbenzene hydroperoxide, paramenthane by hydroperoxide and azoisobutyronitrile and other or light. Suitable solvents are paraffine as pentane, hexane, heptane, octane and isoparaffines or cyclic hydrocarbons as cyclopentane, cyclohexane, cycloheptane, cyclooctane and so on or tetraline, decaline, benzene, toluene, xylene and so on. The concentration of the peroxides can be 0,04–0,15%.

After removing the solvent by distillation, the crude reaction product is further distilled or directly processed further. For this purpose, the morpholine or piperidine or their derivatives are provided, heated to 50°–200° C., preferably 100° C. up to the reflux temperature of the respective nitrogen compound, and the bromine compound (IV) or a mixture of (IV) and (V) are added.

The reaction can be conducted in case in the presence of a solvent but it is not necessary. The excess of the morpholine or piperidine derivates can be as a solvent.

Suitable morpholine or piperidine derivatives are cis-2,6-dimethyl-, trans-2,6-dimethyl- and cis-2,6-diethyl-, trans-2,6-diethylmorpholine, etc. The molar ratio of nitrogen compound to bromine compound IV and V as mixture can range widely, e.g., from 2:1 to 20:1, preferably 2.1:1 to 5:1.

In this step of the process, 1 mole of the nitrogen compound serves for binding the thus-formed hydrogen bromide. Depending on the temperature, the reaction time can range from several minutes to 3 hours or longer.

After the reaction the excess nitrogen compound is removed by distillation, sodium hydroxide solution is added to release additional nitrogen compound from the hydrogen bromide and to remove it likewise by distillation. Optionally, a solvent is added, such as, for example, toluene, xylene, ethylbenzene, diethylbenzene, etc., and the thus-formed sodium bromide is washed out with water. The oil phase is worked up by distillation.

Without further elaboration, it is believed that one skilled in the art can, using the proceding description; utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire text of all applications, patents and publications, if any, cited above and below are hereby incorporated by reference.

EXAMPLE 1a

A glass apparatus is used consisting of a three-necked flask with gas feed tube, stirrer, thermometer, dropping funnel, and reflux condenser.

Starting material:

| | | |
|---|---|---|
| 198 g (= 1.5 moles) | of | methallylbenzene (98.5% strength) |
| 666 g | of | hexane |
| 10.8 g | of | dibenzoyl peroxide (70% strength) |

A solution of these compounds is cooled with a cold water bath to 10° C., and gaseous hydrogen bromide is introduced up to saturation.

After removing the solvent by distillation under normal pressure, the reaction product is distilled at 0.5–0.8 mbar. Boiling range 65°–72° C.; distillate quantity 291 g, content, according to GC analysis: 91.9%. Yield of 1-phenyl-2-methyl-3-bromopropane 83.7% of theory, based on feed.

EXAMPLE 1b

A glass apparatus is employed consisting of a three-necked flask with stirrer, thermometer, dropping funnel, and attached distillation column with distillation device.

Starting material:

| | |
|---|---|
| 345.6 g (= 3 moles) of | cis-2,6-dimethylmorpholine (95.7% strength) |
| 213.1 g (= 0.919 mole) of | 1-phenyl-2-methyl-3-bromopropane (91.9% strength) from Example 1a |

The 2,6-dimethylmorpholine is heated to boiling under reflux, the prevailing temperature being 142° C. Within one-half hour, the bromine compound is added dropwise and the mixture heated to boiling for another 2 hours under reflux. During this step, the temperature rises to 158° C.

Then the mixture is cooled to 112° C., and 88 g (=1.1 moles) of sodium hydroxide solution (50% strength) is added. At this point in time, cis-2,6-dimethylmorpholine is removed by distillation and, to the extent that distillate is obtained, 300 g of diethylbenzene is added as the solvent or suspension agent, and distilled. Thereafter, the mixture is cooled off, the thus-formed sodium bromide is washed out with water, and the oil phase is worked up by distillation. At 1.3 mbar, in a boiling range from 121° to 123° C., 201 g distillate is obtained having a content of 98.0% which, according to NMR spectrum, is the expected 4-(3-phenyl-2-methyl-propyl)-cis-2,6-dimethylmorpholine (Formula I). The yield is 86.3%, based on the feed material.

EXAMPLE 2a

The glass apparatus described in Example 1a is used, and isobutenylbenzene is employed in place of methallylbenzene. The process is conducted as described in Example 1, except that distillation of the bromine compounds is omitted due to low thermal stability. After removing the solvent by distillation, there remains 294 g of residue. According to NMR analysis, the primary product is, to an extent of 80–90%, 1-phenyl-2-methyl-2-bromopropane, and GC analysis shows a main peak with 87.5%. The yield of this tertiary bromine compound is calculated to be 80.5% of theory, based on feed.

EXAMPLE 2b

The glass apparatus described in Example 1b is employed, and the tertiary bromine compound obtained in Example 2a is used in place of the primary bromine compound disclosed therein. The process is performed as described in Example 1b.

During distillatory processing, the contrast to the result in Example 1b, no product is obtained in the boiling range of interest, but merely low-boiling compounds.

EXAMPLE 3a

The glass apparatus set forth in Example 1a is employed, and, in place of methallybenzene, p-tert-butyl-methallylbenzene is used with a content of 98.0% and a content of p-tert-butylisobutenylbenzene of 0.4%.

The process is conducted as described in Example 2a. After removing the solvent by distillation, the distillation residue contains, according to GC analysis, a primary component of 88.0% which is, according to NMR spectrum, 3-(p-tert-butylphenyl)-2-methyl-1-bromopropane. The yield of this bromine compound is calculated to be 90.5% based on feed.

EXAMPLE 3b

The glass apparatus is used which is described in Example 1b, and the product obtained in Example 3a is employed in place of the bromine compound set forth therein. The process is performed as described in Example 1b.

Working up by distillation yields, in a boiling range of 149°–155° C. at 0.8 mbar, the desired morpholine derivative cis-4-[3-(p-tert-butylphenyl)-2-methylpropyl]-2,6-diemthylmorpholine, the structure (I) of which is confirmed by NMR spectrum, in a 98.2% purity. The yield of (1) is 89.4% of theory, based on feed.

EXAMPLE 4a

The apparatus described in Example 1a is utilized, and, instead of methallylbenzene, a mixture is used having a concentration of 97.6% and consisting of 71.2% p-tert-butylmethallylbenzene and 26.4% p-tert-butylisobutenylbenzene.

The process is performed as described in Example 2a. The solvent-free distillation residue contains, according to GC analysis, two primary components with contents of 31.6% and 57.7%. According to the NMR spectrum, the main component is 3-(p-tert-butylphenyl)-2-methyl-1-bromopropane, and the secondary component is the corresponding tertiary bromine compound.

The total yield of bromine compounds is 86.8% of theory, based on feed, and the yield of primary bromide is 76.9% of theory, based on the proportion of starting alpha-olefin.

EXAMPLE 4b

The glass apparatus is used which is described in Example 1b, and in place of the bromine compound set forth therein, the product mixture is used obtained in Example 4a. The process is conducted as described in Example 1b. The purity of the distilled morpholine derivative is 98.3%.

The yield of cis-4-[3-(p-tert-butylphenyl)-2-methylpropyl]-2,6-dimethylmorpholine (I) is 75.8% of theory, based on starting p-tert-butylmethallybenzene in Example 4a or, expressed differently: 1.068 moles of this alpha-olefin yield 0.81 mole of morpholine derivative. In addition, 0.22 mole of alpha-olefin and 0.29 mole of beta-olefin are produced whereas only 0.40 mole of beta-olefin was used in Example 4a. A small proportion of the primary bromine compound thus yields olefins.

EXAMPLE 5

The glass apparatus disclosed in Example 1b is used, and, in place of the cis-2,6-diemthylmorpholine indicated therein, 3 moles of piperidine is employed. The process is conducted as described in Example 1b. During boiling under reflux in the reactor, temperatures are obtained of 98°–104° C., and during the introduction of the bromine compound, the temperatur rise to 113° C.

The thus-formed 3-phenyl-2-methylpropyl-cis-2,6-dimethylpiperidine (Formula I) boils at 128°–130° C. under 2.7 mbar. The purity of the distillate is 98.5%, and the yield is 79%, based on starting material.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the production of N-substituted morpholines and piperidines of the formula

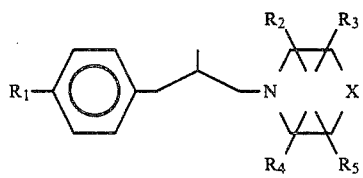

comprising the steps of
(a) reacting a methallylbenzene of the formula

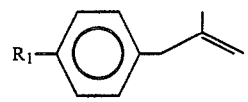

wherein $R_1$ is H or a straight or branched chained $C_1$-$C_4$ alkyl group, alone or in admixture with a corresponding isobutenylbenzene of the formula

wherein $R_1$ is as defined above, with hydrogen bromide in the presence of a peroxide to yield, respectively, the corresponding bromine compound of the formula

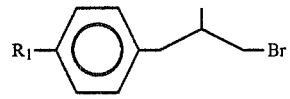

wherein $R_1$ is as defined above, alone or in admixture with a bromine compound of the formula

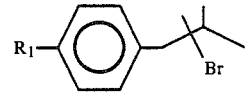

wherein $R_1$ is as defined above and wherein the bromine atom is on the secondary or tertiary carbon atom thereof, and (b) reacting the resultant bromine compound of formula IV, alone or in admixture with the corresponding bromine compound of Formula V, with a morpholine or piperidine compound of the formula

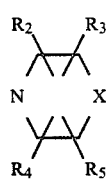

wherein $R_2$, $R_3$, $R_4$ and $R_5$ are each independently hydrogen, methyl or ethyl and X is as defined above.

2. The process of claim 1, wherein step (b) is conducted at a temperature of from about 50° to about 200° C.

3. The process of claim 2, wherein step (b) is conducted at a temperature of from about 100° C. up to the reflux temperature of the compound of formula VI.

4. The process of claim 1, wherein in step (b) the molar ratio of the morpholine or piperidine compound to the bromine compound or compounds is from about 2:1 to 20:1.

5. The process of claim 4, wherein said molar ratio is from about 2.1:1 to about 5:1.

6. The process of claim 4, wherein step (b) is conducted at a temperature of from about 50° to about 200° C.

7. The process of claim 6, wherein said molar ratio is from about 2.1:1 to about 5:1.

8. The process of claim 1, wherein the compound of Formula VI is morpholine, 2,6-dimethylmorpholine, cis-2,6-diethylmorpholine, piperidine, trans-2,6-diethylmorpholine, piperidine or 2,6-diethylpiperidine.

9. The process of claim 2, wherein the compound of Formula VI is morpholine, 2,6-dimethylmorpholine, cis-2,6-diethylmorpholine, piperidine, trans-2,6-diethylmorpholine, piperidine or 2,6-diethylpiperidine.

10. The process of claim 3, wherein the compound of Formula VI is morpholine, 2,6-dimethylmorpholine, cis-2,6-diethylmorpholine, piperidine, trans-2,6-diethylmorpholine, piperidine or 2,6-diethylpiperidine.

11. The process of claim 4, wherein the compound of formula VI is morpholine, 2,6-dimethylmorpholine, cis-2,6-diethylmorpholine, piperidine, trans-2,6-diethylmorpholine, piperidine or 2,6-diethylpiperidine.

12. The process of claim 5, wherein the compound of Formula VI is morpholine, 2,6-dimethylmorpholine, cis-2,6-diethylmorpholine, piperidine, trans-2,6-diethylmorpholine, piperidine or 2,6-diethylpiperidine.

13. The process of claim 1, wherein said peroxide is dibenzoyl peroxide.

14. The process of claim 1, wherein X is $=O$.

15. The process of claim 1, wherein X is $CH_2$.

* * * * *